| United States Patent [19] | [11] | 4,429,050 |
|---|---|---|
| Yasuda et al. | [45] | Jan. 31, 1984 |

[54] COMPETITIVE IMMUNOCHEMICAL MEASUREMENT OF PLURAL TRACE COMPONENTS INVOLVING SPECTRAL SENSITIZING DYE LABELS

[75] Inventors: Yukio Yasuda; Nobuhito Masuda; Yuji Mihara; Masaki Okazaki, all of Minami-ashigara; Nobuo Hiratsuka, Tokyo, all of Japan

[73] Assignee: Fuji Photo Film Co., Ltd., Tokyo, Japan

[21] Appl. No.: 298,811

[22] Filed: Sep. 2, 1981

[30] Foreign Application Priority Data

Sep. 2, 1980 [JP] Japan ................................ 55-120593

[51] Int. Cl.$^3$ ..................... G01N 33/54; G01N 33/58; G01N 33/52; G01N 33/74
[52] U.S. Cl. .................................... 436/538; 430/566; 430/631; 436/539; 436/541; 436/544; 436/546; 436/800; 436/805; 436/817
[58] Field of Search .................. 23/230 B, 915; 424/8, 424/12; 435/7; 430/566; 436/538, 539, 541, 544, 546, 800, 805, 817

[56] References Cited

U.S. PATENT DOCUMENTS

| 3,952,091 | 4/1976 | Grunberg | 23/230 B X |
|---|---|---|---|
| 4,331,444 | 5/1982 | Mihara | 23/230 B |
| 4,337,063 | 6/1982 | Mihara | 23/230 B |
| 4,337,065 | 6/1982 | Hiratsuka | 23/230 B |

*Primary Examiner*—Sidney Marantz
*Attorney, Agent, or Firm*—Sughrue, Mion, Zinn, Macpeak & Seas

[57] ABSTRACT

A method for the simultaneous immunochemical assay of trace components in a sample involving competitively reacting the antigens or antibodies in a sample and labeled antigens or labeled antibodies for limited binding sites. The labels are spectral sensitizing dyes. The reaction products are contacted with silver halide and exposed to light having wavelengths corresponding to the absorption spectra of the spectral sensitizing dyes.

6 Claims, 3 Drawing Figures

COMPETITIVE IMMUNOCHEMICAL MEASUREMENT OF PLURAL TRACE COMPONENTS INVOLVING SPECTRAL SENSITIZING DYE LABELS

BACKGROUND OF THE INVENTION

1. Field of the Invention

This invention relates to a method for the immunochemical measurement of trace components and particularly to a method for the immunochemical measurement of trace components.

2. Development of the Invention

Radioimmunoassay (hereafter merely "RIA") is a method for the assay of a trace component utilizing a specific antigen-antibody reaction. The basic principles of RIA are as follows. The reaction of a substance labelled or marked with a radioactive isotope (RI) in a given amount and a substance having a specific binding afffinity thereto in a given amount results in a coupled product of both of these components, while a part of the labelled substance remains in an unbound or unreacted free state. The reaction proceeds based on the laws of mass action in general, and, therefore, when an unlabelled substance is added to the reaction system, binding with a limited amount of binding protein is decreased and a certain relationship (calibration curve) can be established therebetween. As a result, an amount of an unknown substance can be determined from the calibration curve if the bound substance and the labelled substance in the free state are separated and either one or both are measured with respect to the RI amount.

Due to the high sensitivity and the simplicity of RIA, RIA is particularly applicable to the measurement and inspection of trace amounts of proteins in blood and hormones. Details thereon are given in, e.g., Kumahara and Shizume, NEW RADIOIMMUNOASSAY, pages 3 to 10 (1977), published by Asakura Publishing Co., Ltd., Tokyo, KISO SEIKAGAKU JIKKENHO (Basic Biochemical Experiments) (6), subtitled "Biochemical Assay" (1967), published by Maruzen Co., Ltd., Tokyo, P. D. Boyer et al, *The Enzyme*, vols. 3, 4 and 5 (1971), published by Academic Press, New York, and METHODS IN ENZYMOLOGY, edited by Sidney P. Colowick et al, vols. I, II, III, V and VII, published by Academic Press, New York.

However, RIA is subject to several disadvantages due to the use of RI labelling substances ($^{125}$I, $^{131}$I, etc.) which must have high specific radioactivity to maintain immune activity and must be of high purity. For these reasons, RIA involves the danger of radiation exposure and it is necessary to use expensive and unstable labelling substances which cannot be used for extended periods of time. In addition, special installations, equipment and personnel qualified to deal with radiation are required. Finally, after RIA, disposal of radioactive waste material and the ensuing pollution problems are encountered.

Further, in the case that analysis of a plurality of trace components in blood is to be used for making a diagnosis of a disease or for determining the condition of a disease, it is difficult to measure all such components at the same time in the same reaction system per the RIA method. To detect plural components, a number of examinations equal to the number of components must be carried out individually for each component and, therefore, it is necessary to increase the volume of blood examined according to the number of components. Obviously, an increase in the volume of blood taken is undesirable for young children or the weak.

In short, it has been substantially impossible to simultaneously measure a plurality of trace components in the same reaction system without increasing the volume of blood taken because each component cannot be labelled by different substances per the RIA method.

SUMMARY OF THE INVENTION

An object of this invention is to provide a method for the immunochemical measurement of trace components which does not involve harmful radiation, which may be used for long periods of time and which does not require expensive measuring devices.

Another object of this invention is to provide a method for the immunochemical measurement of trace components by which plural kinds of components can be measured simultaneously in the same reaction system without increasing the volume of blood taken for analysis.

This invention provides a method for the immunochemical measurement of trace components contained in a solution, which comprises labelling an antigen or antibody with a spectral sensitizer having an absorption region of a wavelength longer than the intrinsic absorption wavelength of silver halide (preferably longer than 500 nm) which is adsorbed onto silver halide grains to spectrally sensitize the same, immunochemically reacting the labelled substance with an antibody or antigen, bringing either the reaction product or the unreacted antigen or antibody into contact with silver halide, then exposing the same, developing the exposed silver and then measuring the quantity of the resulting developed silver or colored dye as optical density.

BRIEF DESCRIPTION OF THE DRAWINGS

FIG. 1 is an enlarged section of a coated film for measurement according to this invention wherein:

Figure 1:
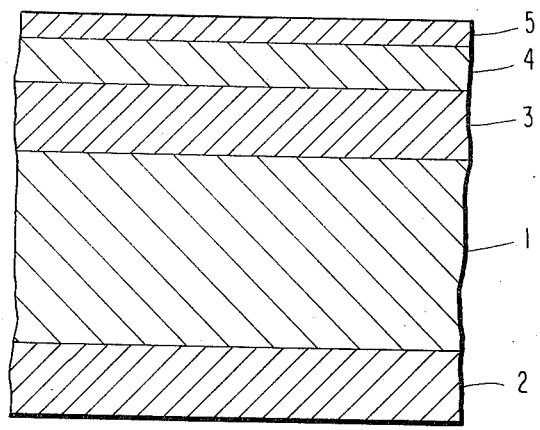

numeral 1 is substrate, numeral 2 is an optical filter, numeral 3 is a subbing layer, numeral 4 is an emulsion layer and numeral 5 is a filter layer.

Figure 2:
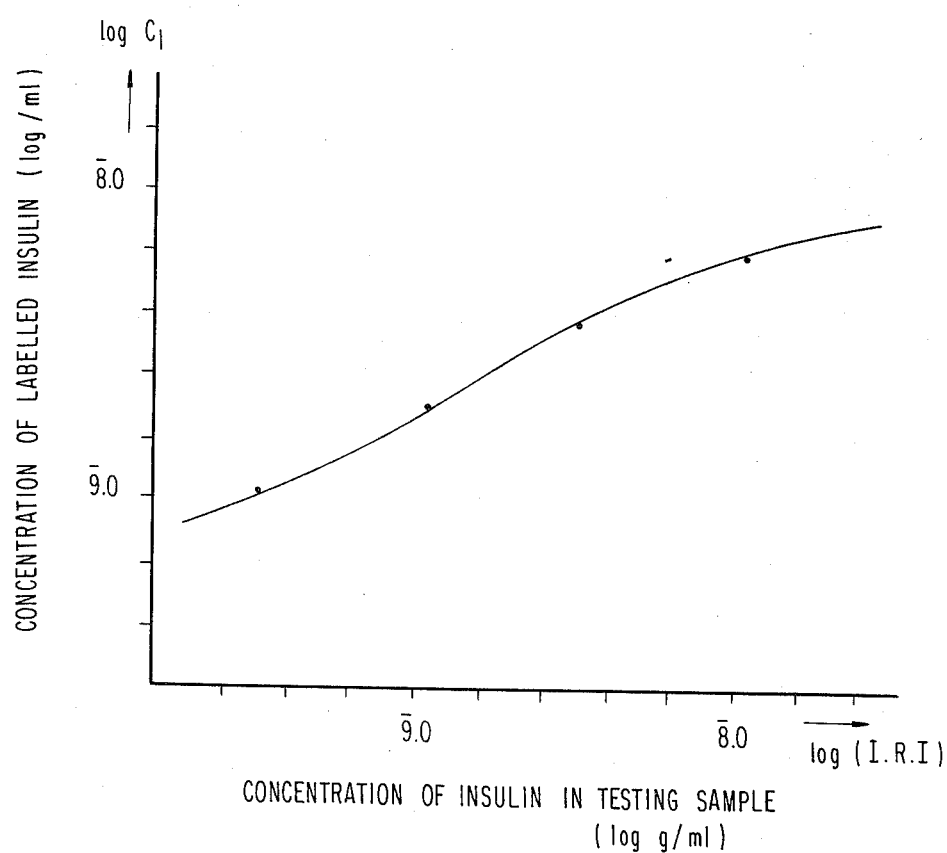

FIG. 2 shows a calibration curve for insulin. Logarithmic values of labelled insulin concentration (g/ml) are shown on the ordinate and logarithmic values of insulin concentration in a testing sample (g/ml) are shown on the abscissa.

Figure 3:
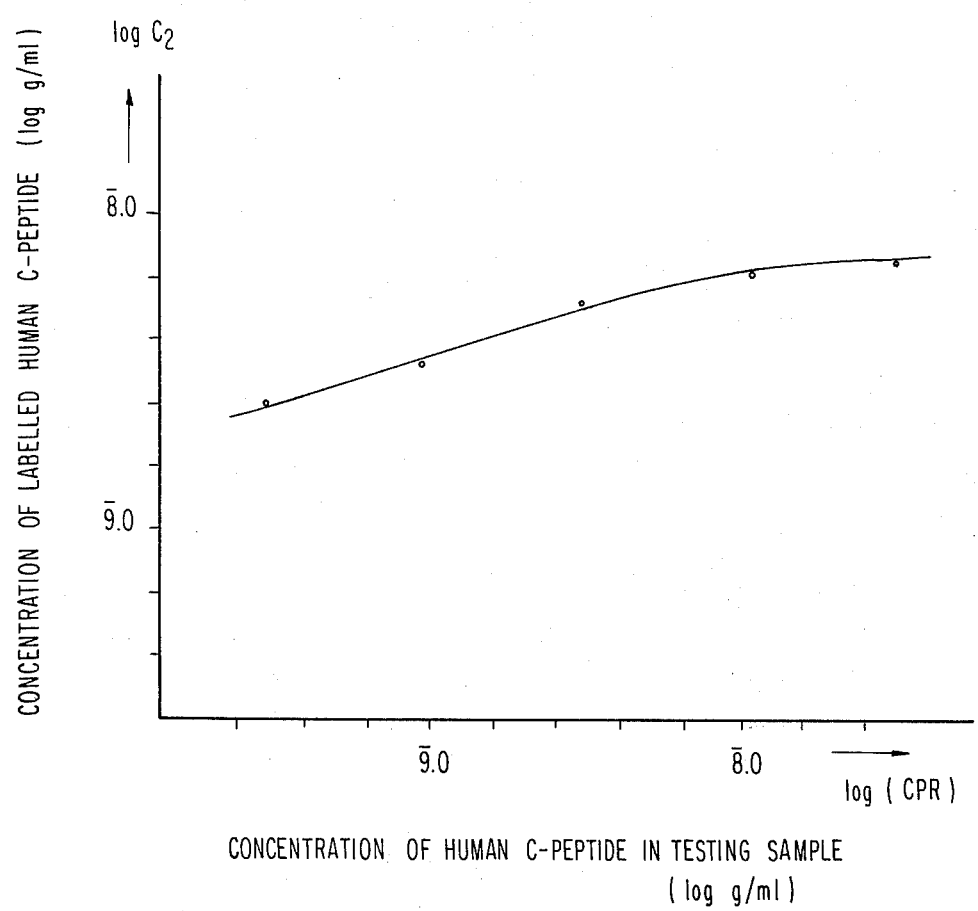

FIG. 3 shows a calibration curve for human C-peptide. Logarithmic values of labelled human C-peptide concentration (g/ml) are shown on the ordinate and logarithmic values of human C-peptide in a testing sample (g/ml) are shown on the abscissa.

DESCRIPTION OF THE PREFERRED EMBODIMENTS

In the method of this invention, each antigen or antibody is labelled with a dye having, of course, an individual spectral sensitization wavelength, a testing sample containing plural kinds of antigens or antibodies to be analyzed is added to the mixture of plural kinds of labelled antigens or antibodies to effect a competitive reaction between each antigen or antibody and a specific antibody or antigen reactive with said each antigen or antibody. Either the reaction product or the remaining unreacted substance(s) is supplied by spotting in plural places on a layer containing silver halide and is then exposed to the light at each spectral sensitization wavelength to which said individual dyes are sensitive, developed, and the density of each exposed area is measured. Calculation of the density value of each of area exposed to light of a different wavelength enables the quantity of each kind of antigen or antibody to be measured with ease. The simultaneous measurement of plural kinds of antigens or antibodies in accordance with this invention is explained below in more detail with reference to a specific example. For instance, the simultaneous measurement of this invention is typically carried out as follows:

(1) Insulin labelled with spectral sensitizer (I) and human C-peptide labelled with spectral sensitizer (II) which produces spectral sensitization different from spectral sensitizer (I) are prepared for the labelled antigens.

(2) Anti-insulin antibody having specific reactivity directed to both natural insulin (in sample serum) and labelled insulin is prepared. Anti-human C-peptide is also prepared as in the case of insulin.

(3) Two antigen-antibody reactions are competed as follows: A known volume of insulin present in sample serum and human C-peptide are added to a known volume of a buffer solution. Known amounts of labelled insulin and a known amount of labelled human C-peptide are added to the above mentioned buffer solution. Then, known amounts of anti-insulin antibody solution and anti-human C-peptide antibody solution are added to the above mixtures. The mixtures are incubated for a time period necessary for completing competitive antigen-antibody reactions; i.e., the reaction between anti-insulin antibody and natural insulin or labelled insulin, the reaction between anti-human C-peptide antibody and natural C-peptide or labelled C-peptide.

(4) The reaction mixture is separated into the insoluble residue and the supernatant in a conventional manner such as centrifuge, solid phase second antibody, or by adding precipitating agents, e.g., polyethylene oxide. Two portions of the supernatant which contain the unreacted labelled antigens varying each concentration of antigens in sample serum are supplied on a silver halide emulsion-coated film in the dark. Both of the labelled antigens present at the supplied portion migrate into a silver halide emulsion layer of the film, where the labelled antigens are adsorbed onto the silver halide grains. The silver halide grains are spectrally sensitized proportionally to each amount of the labelled antigens.

(5) The silver halide emulsion coated film is then exposed to light through an appropriate filter to transmit each light to which the silver halide grains are spectrally sensitized by the dye-labelled antigen. Different filters are used for exposing the two portions supplied on the film. After the exposures, the silver halide emulsion coated film is dipped in a photographic developer which produces reduced silver in the layer from the silver halide grains having adsorbed thereon the dye-labelled antigens. Thus, the reduced silver forms a silver spot and its amount depends upon the adsorbed dye-labelled antigens.

(6) Each amount of silver is directly measured by the optical density of the spotted portion. One set of spectral density values is obtained from one exposed portion through the filter relating to dye (I)-labelled insulin and the other exposed portion through the filter relating to dye (II)-labelled human C-peptide.

(7) Determination of both dye-labelled insulin and dye-labelled human C-peptide is easily done according to the procedure indicated below.

The procedures from (4) to (6) above are repeated using known mixtures of each dye-labelled antigen, instead of using the supernatant. One set of optical density is obtained from each mixture. The method of least squares gives a relation between the concentration of two dye-labelled antigens and optical densities.

(8) Measurement of both insulin and human C-peptide concentration in serum is easily done using a calibration curve as indicated below.

(8-1) Using a testing sample containing a known amount of insulin, procedures (3) to (7) above are repeated. The concentrations of unreacted labelled insulin corresponding to standard insulin having various concentrations are obtained. Relationships as shown in FIG. 2 are useful as calibration curves for measuring unknown insulin concentration in serum.

(8-2) According to the same procedure, the relationship to human C-peptide as shown in FIG. 3 is obtained, which serves for measuring unknown C-peptide concentration in serum.

(8-3) Simultaneous measurement of both insulin and human C-peptide concentration in serum is obtained from each concentration of the unreacted dye labelled antigen by procedure (&) and calibration curves by (8-1) and (8-2).

The spectral sensitizer for photographic use employed for the sensitizer-labelled substance utilized in this invention, for labelling a trace component such as an antigen or antibody possesses the capability to impart spectral sensitization to silver halide. Such spectral sensitizers are known as spectral sensitizers for photographic light sensitive materials and include, e.g., cyanine dues, merocyanine dues, hemicyanine dyes, styryl dyes, etc. These dyes are specifically described in The Theory of the Photographic Process (4th edition), edited by T. H. James (1977), published by Macmillan Co., Ltd., Cyanine Dyes and Related Compounds, F. M. Hamer (1964), Interscience Publishers, etc.

In more detail, merocyanine dyes as described in U.S. Pat. Nos. 2,493,748, 2,519,001 and 2,652,330, German Patent No. 1,177,481 and French Patent No. 1,412,702, cyanine dyes as described in U.S. Pat. Nos. 2,238,213, 2,503,776, 2,537,880, 3,196,017 and 3,397,060, German Patent Nos. 929,080, 1,028,718, 1,113,873, 1,163,671 and 1,177,482, French Patent No. 1,359,683, British Pat. Nos. 840,223, 886,270, 886,271 and 904,332, Belgian Patent No. 654,816 and Japanese Patent Publications 14112/65 and 23467/65 ("patent publication" used in this specification means an application published for purpose of opposition and is available for public inspection), etc., are all effective dyes for this invention.

These dyes can also be employed in combinations of two or more thereof. For example, supersensitization including the use of dyes as described in Japanese Patent Publications 4932/68, 4936/68, 22884/68, etc. is also effective for this invention. Further, supersensitization as described in U.S. Pat. Nos. 2,947,630, 2,933,390, 2,937,089, 3,617,295 and 3,635,721, French Patent No. 1,500,218, etc., is also effective. In this case, the supersensitizing dye combination can be mixed together with the labelled trace components, such as an antigen or antibody, or can be previously incorporated into a silver halide emulsion.

Of these spectral sensitizers, the dyes described below are particularly advantageous as the labelling substance(s) since these dyes are excellent in binding to the trace components such as an antigen or antibody. In this invention, such spectral sensitizers as having an absorption region at a longer wavelength (preferably longer than 500 nm) than the absorption wavelength region intrinsic to silver halide, which spectrally sensitize silver halide grains by contact with (adsorption to) the silver halide grains, are employed.

Preferred spectral sensitizers are described by reference to formulae (I), (II-1), (II-2) and (III) below wherein, unless otherwise indicated, an alkyl group (including a substituent, if any, and also including the alkyl moiety present in an alkoxy group, a dialkylamino group, etc.) generally possesses 1 to 12 carbon atoms, preferably 1 to 5 carbon atoms in total and an aryl group (including a substituent, if any, and also including the aryl moiety present in an aryloxy group, a diarylamino group, etc.) generally possesses 6 to 18 carbon atoms, preferably 6 to 11 carbon atoms.

(1) Cyanine dyes of formula (I) below containing at least one of a mercapto group, an amino group, a hydroxy group or a carboxy group in the heterocyclic nucleus thereof:

In formula (I) above, at least one of $R$, $R_1$, $R_2$ and $Z_1$ contains at least one group selected from the class consisting of a mercapto group, an amino group, a hydroxy group and a carboxy group.

(2) Merocyanine dyes of formula (II-1) below, containing at least one of a mercapto group, an amino group, a hydroxy group and a carboxy group:

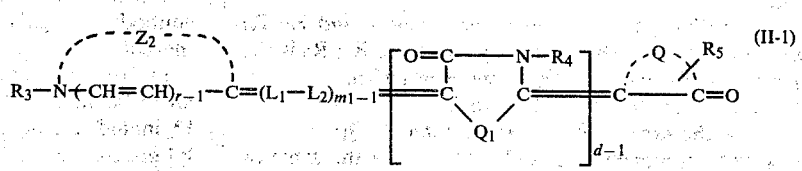

wherein
$Z_2$ has the same meaning as Z and $Z_1$;
$R_3$ and $R_4$ have the same meanings as R and $R_1$; $R_5$ has the same meaning as $R_2$; r has the same meaning as n; $L_1$ and $L_2$ are as defined above;
$m_1$ represents 2, 3 or 4;
d represents 1, 2 or 3;
$Q_1$ represents an oxygen atom, a sulfur atom or —N—$R_6$ ($R_6$ represents an aliphatic group);
Q represents a non-metallic atomic group necessary for completing a 5-membered or 6-membered nitrogen-containing heterocyclic nucleus.

In formula (II-1) at least one of $R_3$, $R_4$, $R_5$ and $R_6$ contains at least one group selected from the class consisting of a mercapto group, an amino group, a hydroxy group and a carboxy group.

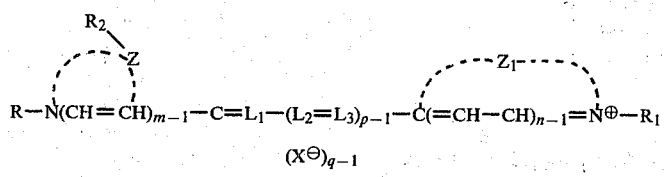

wherein m and n each represents 1 or 2; p represents 2 or 3; q represents 1 or 2' $L_1$, $L_2$ and $L_3$, which may be the same or different, each represents a methine group (which may be substituted with an alkyl group, a halogen atom, an aryl group, etc.); Z and $Z_1$ each represents a non-metallic atomic group necessary for completing a 5- or 6-membered nitrogen-containing heterocyclic nucleus, which may be the same or different; R and $R_1$, which may be the same or different, each represents a substituted or unsubstituted alcohol residue, $R_2$ is a substituent for Z and represents a hydrogen atom or —$P_i$—$Q_j$—W wherein P is

—N—, —N—CO—,
|         |
$R_{20}$  $R_{20}$

—CO—, —O— or —S— [wherein $R_{20}$ represents a hydrogen atom, an alkyl group having 1 to 8 carbon atoms, a substituted alkyl group; Q represents an alkylene group having 1 to 10 carbon atoms or a substituted alkylene group.

(3) Merocyanines dyes having a carboxy-containing substituent on the acidic nucleus and having formula (II-2), which corresponds to the merocyanine dyes of formula (II-1) wherein d is 1 and $=(L_1—L_2)_{m-1}$ is $=(CH—CH)_{p-1}$.

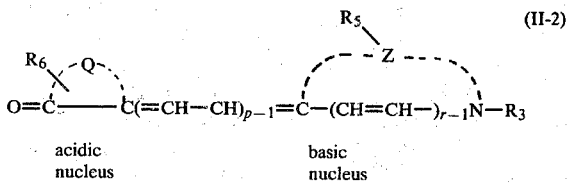

acidic nucleus   basic nucleus wherein r has the same meaning as n as hereinbefore defined, p is 2 or 3; only $R_6$ among $R_3$, $R_5$ and $R_6$ contains at least one carboxy-containing group and all other moieties are as defined for formula (II-1).

(4) Rhodacyanine dyes shown by formula (III) below, containing at least one of a mercapto group, an amino group, a hydroxy group and a carboxy group:

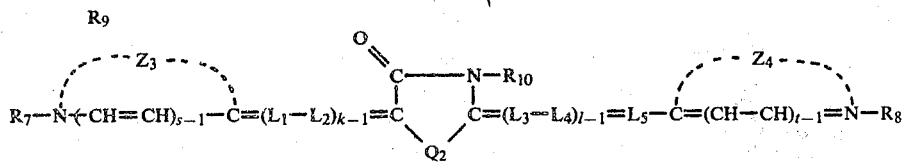

wherein $Z_3$ and $Z_4$ have the same meanings as $Z$ and $Z_1$; $R_7$ and $R_8$ have the same meanings as $R$ and $R_1$; $R_9$ is the same as $R_2$; s and t are the same as m and n;

$L_1$ to $L_5$ are the same as $L_1$ to $L_3$;

$R_{10}$ is the same as $R_4$; $Q_2$ is the same as $Q_1$;

k and l represent 1, 2 or 3, and may be the same or different.

At least one of $R_7$, $R_8$, $R_9$, $R_{10}$ and $Q_2$ contains at least one group selected from the class consisting of a mercapto group, an amino group, a hydroxy group and a carboxy group.

When dissolving an antigen or antibody labelled with the aforesaid spectral sensitizer in the water-containing medium necessary to carry out the antigen-antibody reaction, if a compound of formula (S) below is also present, the labelled substance is stabilized, whereby the objects of this invention are more effectively accomplished.

$$D_1-A-D_2 \qquad (S)$$

wherein $D_1$ and $D_2$ each represents a condensed polycyclic aromatic heterocyclic moiety or an aromatic heterocyclic ring-substituted amino group, which may contain an —$SO_3M$ group, wherein M is a hydrogen atom, an alkali metal or ammonium group, —A— is a divalent aromatic residue which optionally may contain an —$SO_3M$ group where M is as defined above, provided that the —$SO_3M$ group should be present in or substituted on —A— when the —$SO_3M$ group is not present in or substituted on $D_1$ or $D_2$ as the labelled antigen or antibody is highly stable even in an aqueous solution thereof.

In formula (S), examples of the condensed polycyclic aromatic heterocyclic residue represented by $D_1$ and $D_2$ include a 2-benzotriazolyl group, a 2-naphthotriazolyl group, etc.; and examples of the aromatic heterocyclic ring-substituted amino group include a 1,3,5-triazin-2-yl amino group, a 1,3-diamin-2-yl amino group, etc.

Preferred examples of the divalent aromatic groups represented by A are as follows:

Sulfo-Containing Groups:

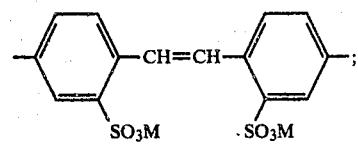

In formula (S), examples of the condensed polycyclic aromatic heterocyclic residue represented by $D_1$ and $D_2$ include a 2-benzotriazolyl group, a 2-naphthotriazolyl group, etc.; and examples of the aromatic heterocyclic ring-substituted amino group include a 1,3,5-triazin-2-yl amino group, a 1,3-diamin-2-yl amino group, etc.

Preferred examples of the divalent aromatic groups represented by A are as follows:

Sulfo-Containing Groups:

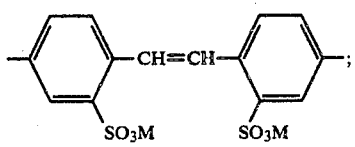

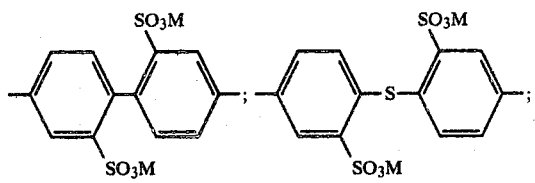

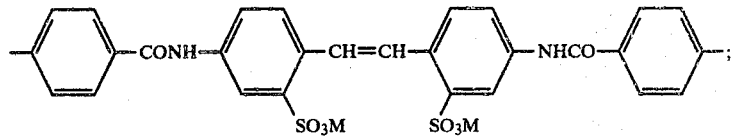

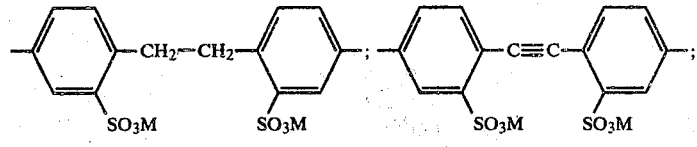

-continued

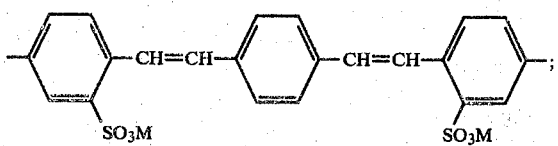

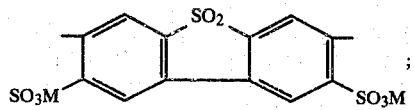

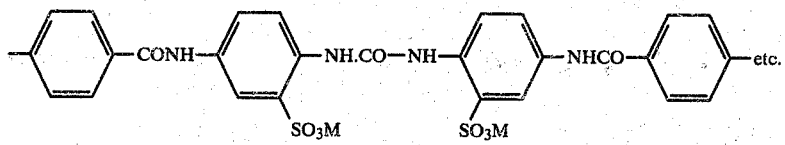

Groups free of a sulfo group:

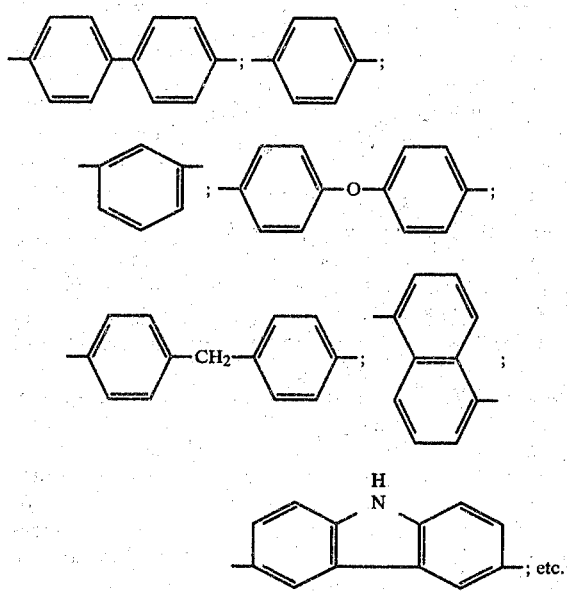

Antigens or antibodies are labelled with spectral sensitizers by an ordinary chemical reaction. Thus, a spectral sensitizer can be reacted with an antigen or antibody to form a labelled reaction product by covalent linkage; specifically, the reaction occurs between the functional group (i.e., mercapto, amino, hydroxy or carboxy) of the spectral sensitizer and an amino, imino, mercapto, carboxy, carboxylic acid amide or hydroxy group(s) of an antigen or antibody. The reaction between the two can be carried out by any of the following procedures:

(1) Spectral sensitizers are directly reacted with the aforesaid functional groups;

(2) Spectral sensitizers and the aforesaid functional groups are reacted using an activating agent, and (3) Spectral sensitizers and the aforesaid functional are reacted through at least one compound having a bifunctional group.

Groups which are reactive with the aforesaid functional groups of antigens or antibodies and methods for reacting the same are described in detail, in, e.g., *Lectures on Experimental Biochemistry*, vol. 1 subtitled "Chemistry of Proteins", ibid., vol. 2, subtitled "Chemistry of Nucleic Acids", ibid., vol. 3 subtitled "Chemistry of Lipids" and ibid., vol. 4, subtitled "Chemistry of Sugars", all edited by the Biochemical Association, Japan, published by Tokyo Kagaku Dojin (1977); Izumiya, PEPTIDE GOSEI (Peptide Synthesis), and Greenstein et al. CHEMISTRY OF THE AMINO ACIDS, vols. I–III (1961), John-Wiley & Sons Inc., New York. One skilled in the art can easily perform such reactions for forming the linking from knowledge in the art and these publications.

Examples of compounds containing groups which react with the aforesaid functional groups further include, e.g., activated esters, activated halogens, aldehydes, activated vinyl esters, activated halogens, aldehydes, activated vinyl compounds, acid anhydrides, acid halides, thioisocyanates, isocyanates, carboxylic acids, amides, alkyl halides, nitrophenyl halides, etc. Accordingly, these functional groups can originally be present in the spectral sensitizer or can be introduced as a result of the reaction of a compound having a bifunctional group and the spectral sensitizer.

Reaction conditions for labelling vary depending upon the kind of the antigen or antibody, the kind of spectral sensitizer, etc., and conditions are selected so as to not damage the biological activity of the antigen or antibody to be labelled. Accordingly, the reaction temperature is generally chosen from the range of from 40° to 60° C., preferably −20° to 40° C.; and the reaction time from the range of from 10 mins. to 16 hrs. The reaction pressure is preferably atmospheric pressure, but can suitably be chosen from the range of 1 to 20 atms. It is advantageous that water or a pH buffer solution be used as a solvent for the labelling. Organic solvents such as DMF (dimethylformamide), methylene chloride, etc. can also be employed. These reaction conditions are common to reaction conditions which are generally applicable to modification of proteins or enzymes and details are described in the publications referred to above.

The amount of spectral sensitizer used for labelling varies depending upon the kind of the aforesaid substances to be labelled, but is generally in a molar ratio of 1/100 to 100 moles per 1 mole of the antigen or antibody, preferably 1/20 to 20 times, more preferably ½ to 2 times, same basis.

As methods for confirming completion of labelling, methods for measuring spectra such as UV, visible rays, IR, mass and NMR spectra, etc., and a method confirming labelling via disappearance of the terminal group at which the labelling substance is to be introduced, are representative. Simple tests will be enough to confirm completion of labelling. Where it is confirmed utilizing absorption spectrum, following completion of the labelling reaction, an absorption spectrum of a separated and purified product is measured; if the resulting absorption spectrum is consistent with the intrinsic absorption spectru which a spectral sensitizer possesses, it is confirmed that the labelling reaction was effected. A further method for confirming the labelling being effected is to analyze for the presence or absence of the specific terminal groups, e.g., an amino or carboxy group(s). In the case that the spectral sensitizer is introduced at the terminal amino group(s) of the spectral sensitizer, it is confirmed by the analysis of the N-terminal that completion of the labelling reaction has been effected if the corresponding amino acid(s) to an amino group(s) on which labelling is to occur are not detectable. Detailed disclosure on such N terminal analysis is described in, e.g., B. S. Hartley and V. Massey, *Biochim. Biophys. Acta,* 21, 58 (1956) (generally referred to as a Dansyl method in the art), *Archn. Biochem. Biophys.,* 22, 475 (1949) (a PTC (phenol isocyanate) method), F. Sanger, *Biochem. J.,* 39, 507 (1945) (a dinitrofluorobenzene method), etc. In a similar manner, the terminal carboxy group(s) are analyzed to check completion of the labelling reaction, details of which are given in, e.g., S. Akabori, K. Ohno and K. Narita, *Bull. Chem. Soc. Japan,* 25, 214 (1952) (generally referred to as a hydrazine decomposition method in the art), H. Matuo, U. Fujimoto and T. Tatuno, *Biochem. Biophys. Res. Comminication,* 22, 69 (1966) (a tritium marking method), etc. Further, details of these terminal determination methods are also given as a review in S. B. Needleman, PROTEIN SEQUENCE DETERMINATION, published by Springer Verlag (Berlin), 1975.

In this invention, the antigen or antibody labelled with a spectral sensitizer or the reaction product of immune reaction between the antigen or antibody and another antibody or antigen is brought into contact with silver halide grains to determine the quantity thereof. The following illustrate specific examples of such determinations:

(1) Dropwise adding a solution containing the material(s) mentioned above to a photographic emulsion containing unexposed silver halide grains made from 100 to 300 g silver per kg-emulsion so as to adsorb the substance on the silver halide grains. The resulting emulsion is charged into a transparent cell, exposed to light of a wavelength for spectral sensitization and then a photographic developer is added to blacken the light sensitive silver halide grains and the optical density is measured.

(2) Dropwise supplying a solution containing the material(s) mentioned above on a photographic emulsion coated layer containing unexposed silver halide grains on a substrate to penetrate the same into the coating and adsorb the material on the silver halide grains contained in the coating. Thereafter, the emulsion coated layer is exposed to light of a wavelength at which the emulsion layer is spectrally sensitized from the front side or rear side of the layer, dipped in a photographic developer to change the exposed grains to developed silver and then optical density is measured.

Method (2) is especially preferred and in a most preferred form comprises "spotting" the solution containing the antigens or antibodies to be measured on the coating in separated spots at least equal in number to the tests required, whereafter each spot is exposed to the light of each wavelength for spectral sensitization and then is brought into contact with a developer so as to blacken the spots followed by measurement of optical density.

According to this invention, unknown quantities of antigens or antibodies can be measured by determining either the labelled substance-containing products obtained by immunochemical reaction between the labelled antigens or antibodies, unknown quantities of antigens or antibodies to be measured and the other antibodies or antigens to be specifically reacted with those antigens or antibodies, of the unreacted labelled substances. For this purpose, any suitable technique can be used by which either the reaction products or the unreacted substances are assayed.

To separate the labelled antigen-antibody reaction product (B) from the labelled free antigen or antibody (F) in method (I) of this invention, various separation techniques conventionally used in the art are employed. Typical examples include liquid chromatography techniques (e.g., gel filtration, ion exchange, partition chromatography, adsorption chromatography including affinity chromatography, microfilter filtration, dialysis, adsorption using cellulose, talc, dextran powder, etc., salting out (separation of precipitated and aggregated matters formed by adding a salt to a system, see, L. Wide and C. A. Gemzell, *Ciba Foundation Colloq. on Endocrinol.,* 14, 296 (1962)), precipitation (separation of crystallized specific protein formed due to a difference of dielectric point, etc., which occurs by changing pH, see, G. M. Brodsky and P. H. Forsham, *J. Clin. Invest.,* 39, 1070 (1960)), centrifugation, crystallization, extraction, solid phase separation, etc. Detailed disclosure of these separation techniques is provided in Kazuo Shizume and Yuichi Kumahara, NEW RADIOIMMUNOASSAY, 1967, published by Asakura Publishing Co., Ltd., Tokyo, DATABOOK OF BIOCHEMISTRY, second separate volume, Chapter 10, edited by the Biochemical Association, Japan, published by Tokyo Kagaku Dojin, 1980, etc. In addition, centrifugal separation, solid phase methods, the two antibodies method, the sandwich method and so on are also useful in this invention.

Of the methods mentioned above, centrifugal separation is preferred because the products obtained by immunochemical reaction are insolubilized in the reaction system to form agglomerates, whereby the product (solid) is easily separated from unreacted substances (liquid) by centrifugal separation.

On the other hand, per the solid phase separation method in which antibodies or antigens to be reacted are in the solid phase prior to the immunochemical reaction, centrifugal separation is not required because only unreacted labelled substances remain in solution. The solid phase may be in the form of a plate, bar or granule.

Further, according to the two antibodies method, in which a second antibody which commonly and specifically reacts with the antigen or antibody is reacted, the reaction products become insoluble and precipitatable so that centrifugal separation is not required, which makes measurement simple and thus this method is also preferred. When an antigen-antibody reaction is carried out between more than one component and each antigen or antibody for each component is measured, it is preferred to use one sort of second antibody which can commonly and specifically react with each of antigens or antibodies, after the competitive reaction is completed.

The fraction containing the unreacted labelled substance(s) obtained by the separation procedure described above is directly dropwise added to the silver halide coated support so as to bring it into contact with the silver halide; in this case, unreacted labelled substances are measured.

Immunochemical reaction products may be measured by the following method. Firstly, one washes the agglomerate several times to remove unreacted labelled substances, adds one or more suitable agglomeration inhibitors such as urea or hydrochloric acid-guanidine to the agglomerate to redissolve the products of the immune reaction and the resulting solution is dropped onto the silver halide coated substrate to bring it into contact with the silver halide. In this case, reacted labelled substances are measured.

If desired, a suitable material such as an anionic or cationic hydrophilic polymer or gelatin containing a hardener can be provided on the top of the silver halide coated support as a filter layer so as to selectively adsorb the products of the immune reaction or the unreacted substances or to inhibit diffusion or penetration of the products of the substances so that the same can be measured without centrifugal separation of the reaction mixture. When the filter layer selectively adsorbs the unreacted substances, reacted and labelled substances are measured while when the filter layer selectively adsorbs the reaction products or inhibits the diffusion or penetration of the reaction product, unreacted labelled substances are measured.

Labelling substances, that is, spectral sensitizers used in the method of this invention, are not radioactive, so they do not lead to radioactive problems as with the radioimmunoassay method. Accordingly, assay can be performed without a license to handle radioactive substances and the labelling substances can be stored for long times due to their excellent stability. In addition, an optical densitometer as is ordinarily used for the measurement of photographic images can be used for optical density determinations in this invention whereby measurement can be carried out conveniently and at low cost.

Optical density can essentially be measured by inserting a suitable color filter in the measurement light path. The optical density of a dried film after ordinary photographic processing can be immediately measured or, alternatively, after developing, stopping or fixing, the optical density of the wet film can be measured.

When a spectral sensitizer is brought into contact with silver halide grains, the presence of a hydrazine compound of formula (C) increases detection sensitivity of the silver halide.

wherein $R^1$ is an aryl group which may be substituted, $R^2$ is a hydrogen atom, an alkyl group which may be substituted or an aryl group which may be substituted. Details and the "presence state" of such hydrazine compounds are described in copending U.S. Ser. No. 298,815 filed Sept. 2, 1981.

Trace components which can be assayed by the method of this invention are typically trace components in the living body; drugs, in addition thereto, those amenable to analysis.

Examples of such trace components include peptide hormones (e.g., insulin, glucagon, parathyroid hormone, carcitonin, erythoropoetin, secretin, cholecystokinin, gastrin, angiotensin II, vasopressin, oxytocin, melanocyte-stimulating hormone, adrenocorticotropic hormone, growth hormone, prolactin, luteinizing hormone, follicle-stimulating hormone); non-peptide hormones (e.g., steroid hormones such as glucocorticoid, aldosterone, adrenergic androgene, estrogene, progesterone, testosterone), or other hormones such as thyroid hormones (e.g., thyroxine, triiodothyronine), cortisol, estriol, adrenaline, noradrenaline, melatonine, acetylcholine, enzymes, e.g., lysozyme, $C_1$ esterase, alkali phosphatase, pepsinogen, trypsin, kinase, virus, specific antigens, tumor antigens, e.g., α-fetoprotein, serum protein components, e.g., thyroxine-bound globulin, 2-microglobulin, IgG, IgE, IgM, IgA, human lysozyme; drugs (e.g., LSD, etc.); and others (e.g., rheumatism factor, $B_s$ antigen, $B_s$ antibody, myosin, etc.).

These substances and derivatives thereof which have an immune reactivity equivalent to that of these substances and which are derived the natural products or synthesized can be used to prepare these substances labelled with a spectral sensitizer.

According to this invention, more than one of the trace components mentioned above such as a peptide hormone(s), non-peptide hormone(s), enzyme(s), virus, specific antigen(s), tumor antigen(s), serum protein component(s) and a drug(s) can be combined and an immune reaction carried out in the same reaction system with measurement or analysis of components as described.

In this invention, plural kinds of antibodies or antigens are generally premixed or individually prepared, and then added to immunochemically react with plural kinds of corresponding labelled antigens or antibodies. In this case, it is preferred that there be little or no interaction between antibodies or between antigens in the reaction system. For example, in the system in which insulin and human C-peptide are simultaneously analyzed, it is preferred that the anti-insulin serum and anti-human C-peptide serum used in the system do not interact with each other. It is also preferred that suitable anti-serums be combined to have, if any, poor interaction between insulin and anti-human C-peptide serum and between human C-peptide and anti-insulin serum.

Dyes having different spectral sensitizing wavelengths for labelling more than one antigen or antibody are combined so that the spectral sensitizing wavelength ranges for any one individual antigen or antibody overlap that of any other not at all or over as narrow a wavelength region as possible to decrease error. For example, it is preferred if one combines two sensitizing dyes to use one having a light sensitive maximum wavelength longer than 630 nm and another having one shorter than 630 nm, the difference between the two maximum wavelengths being more than 50 nm. When three days are used, it is preferred to use an additional third sensitizing dye having an exposure light having a wavelength longer than 750 nm which would effect the third sensitizing dye only, but never affect the first and second sensitizing dyes.

To measure, for example, each of two kinds of antigens or antibodies according to this invention, the following methods are useful for exposing, e.g., the light sensitive silver halide emulsion layer.

Per the first method, at least one drop of the competitive reaction product or the remaining unreacted substance(s) is dropped in two places on the light sensitive silver halide emulsion coating, one of the two resulting areas is exposed through a filter having maximum wavelength transmission in the 500 nm to 630 nm range while the other is exposed through a filter having a maximum wavelength transmission longer than 630 nm, whereafter both areas are developed and the optical density of the areas where drops were placed is measured. Calculation of the optical density gives each quantity of two kinds of antigens or antibodies.

According to the second method, in a similar fashion at least one drop—in this instance two drops—of the competitive reaction product or the remaining unreacted substance(s) is dropped, the first area of dropping is exposed through a filter transmitting light of a wavelength longer than 500 nm, and the other is exposed through a filter transmitting light of a wavelength longer than 630 nm, both are then developed and the optical density of the two areas measured to give the quantity of the two kinds of antigens or antibodies from a precalibrated calibration curve.

It is desirable to use a transparent film as the support for the silver halide prepared from, for example, cellulose acetate or a polyester and to expose from the back surface of the emulsion coated layer.

Once the compound labelled with a sensitizing dye penetrates into the coated layer and contacts (is adsorbed on) the coated silver halide emulsion grains, the coated layer becomes sensitive to light of a wavelength in the wavelength range which the spectral sensitizer absorbs. The coated layer is also sensitive to light in the range intrinsic to the silver halide emulsion (generally shorter than 500 nm). Sensitivity in this wavelength range is not affected by the presence of spectral sensitizer. Accordingly, during exposure of the coated layer, it is necessary to cut light of a wavelength of shorter than 500 nm.

A coated layer on which more than one spectral sensitizer is adsorbed must be exposed to light of a wavelength which each of the two spectral sensitizer absorbs, so that an exterior filter is used between the coated layer and the light source. It is also convenient to provide an interior filter between the emulsion layer and the light source, that is, a light absorbing layer which is permeable to at least the light of the spectral sensitizing wavelength and which absorbs light of other wavelengths, especially in the wavelength range to which the silver halide emulsion is intrinsically sensitive. The light absorption layer can be any coated layer between the emulsion layer and the substrate, a dyed substrate itself, or any coated layer on the substrate between the source of exposing light and the sliver halide emulsion.

Methods for the preparation of silver halide emulsions as can be used herein are given in, for example, Trivelli & Smith, *The Photographic Journal*, vol 79, pp. 330 to 338 (1939); C. E. K. Mees, *The Theory of the Photographic Process*, Macmillan Publishing Co., Ltd.; Glafkidis, *Photographic Chemistry*, vol. 1, pp. 327 to 336, Fountain Press, etc.

The silver halide used in this invention can be any one of silver chloride, silver chlorobromide, silver bromide, silver iodobromide, silver chloroiodobromide, or silver iodide. The silver halide of the emulsion used in this invention may be conventional or smaller. It is thus generally preferred that the averange grain diameter be 0.04 to 4 microns (e.g., by measurement of number average by the projected area method).

Methods for forming the silver halide grains include the single jet, double jet, conversion and controlled double jet methods, the last one comprising forming the grains with control of pAg during formation.

The silver halide emulsions employed in this invention are not chemically ripened but generally are chemically sensitized in a conventional manner, for example, by gold sensitization (as disclosed in U.S. Pat. Nos. 2,540,085, 2,597,876, 2,597,915 and 2,399,083, etc.), by sensitization with metal ions of Group VIII of the Periodic Table, by sulfur sensitization (as disclosed in U.S. Pat. Nos. 1,574,944, 2,278,947, 2,440,206, 2,410,689, 3,189,458 and 3,415,649, etc.), by reduction sensitization (as disclosed in U.S. Pat. Nos. 2,518,698, 2,419,974 and 2,983,610, etc.), or by a combination thereof.

Specific examples of chemical sensitizers include sulfur sensitizers such as allylthio carbamide, thiourea, sodium thiosulfate, cystine, etc.; noble metal sensitizers such as potassium chloroaurate, aurous thiosulfate, potassium chloropalladate, etc.; reduction sensitizers such as stannous chloride, phenylhydrazine, reductone, etc.; polyoxyethylene derivatives as described in British Pat. No. 981,470, Japanese Patent Publication 31-6475 and U.S. Pat. No. 2,716,062, etc.; polyoxypropylene derivatives, quaternary ammonium-containing derivatives, etc.

Silver halide emulsions which are employed in this invention can also contain suitable antifoggants and stabilizers. For example, specific antifoggants and stabilizers include thiazolium salts as described in U.S. Pat. Nos. 2,131,038 and 2,694,716, etc.; azaindenes as described in U.S. Pat. Nos. 2,886,437 and 2,444,605, etc.; urazoles as described in U.S. Pat. No. 3,287,135, etc.; sulfocatechols as described in U.S. Pat. No. 3,236,652, etc.; oximes as described in U.S. Pat. Nos. 2,403,927, 3,266,897 and 3,397,987, etc.; nitron; nitroindazoles; polyvalent metal salts as described in U.S. Pat. No. 2,839,405, etc.; thiuronium salts as described in U.S. Pat. No. 3,220,839, etc.; salts of palladium, platinum and gold as described in U.S. Pat. Nos. 2,566,263 and 2,597,915, etc.

Silver halide emulsions which are used in this invention can also contain, if desired, one or more developing agents (e.g., hydroquinones, catechols, aminophenols, 3-pyrazolidones, ascorbic acid or derivatives thereof, reductones, phenylenediamines, etc.), or combinations of these developing agents. The developing agents can be incorporated into a light sensitive emulsion and/or other suitable layers (e.g., a hydrophilic binder layer) of a photographic element. The developing agents can be incorporated using a suitable solvent or in the form of a dispersion as described in U.S. Pat. No. 2,592,368 or French Pat. No. 1,505,778. The light sensitive coated film containing such developing agent(s) may be developed, after exposure, not only by conventional photographic developers but also by a processing solution (alkali activator) from which a developing agent is excluded.

In this invention, as a binder for the silver halide emulsion layer coated on a support, ordinary gelatin (i.e., alkali-treated gelatin or acid-treated gelatin) is usually used. Furthermore, the gelatin may be partially or wholly replaced with another film-forming high molecular weight material. As such a high molecular weight material, there are used materials which do not have a harmful influence on the light sensitive silver halide emulsion, since as albumin, agar agar, gum arabic, alginic acid, acylated gelatin (e.g., phthalated gelatin, malonated gelatin, etc.), a homopolymer or a hydrophilic vinyl compound (e.g., vinyl alcohol, vinylpyrrolidone, acrylamide, styrenesulfonic acid, acrylic acid, etc.) or copolymers containing these vinyl compounds, cellulose compounds (e.g., hydroxyethyl cellulose, carboxymethyl cellulose, dextran, etc.), water-soluble starch, etc. Other layers (e.g., a filter layer, subbing layer, etc.) than the silver halide emulsion layer may contain such a film-forming high molecular weight material as in the silver halide emulsion layer.

A variety of light sources can be employed for exposing the silver halide brought into contact with the spectral sensitizer. In any case, only light having a wavelength(s) that the spectral sensitizer alone absorbs is employed for exposure, excluding wavelength in the absorption region intrinsic to silver halide. A suitable exposure degree is generally from $10^1$ to $10^{10}$ cms. As light sources, for example, a tungsten lamp, a halogen lamp, a mercury lamp, a xenon lamp, etc. can be employed in combination with a suitable optical filter (e.g., a sharp cut filter manufactured by Fuji Photo Film Co., Ltd.). In addition, a solid laser (e.g., a ruby laser, etc.), a semiconductor laser (e.g., a lead sulfide laser, etc.), a dye laser, a gas laser (e.g., a neon helium laser, an argon laser, etc.) and the like can be advantageously employed.

The development performed in this invention can be by the following manner. That is, when a silver halide emulsion is formed on a support, a development process as is conventionally used for the development of photographic materials can be used. Also, the photographic development can be performed by spreading, coating, impregnating or spraying a photographic developing composition onto the silver halide emulsion layer formed on the support. Furthermore, when the silver halide emulsion is in the liquid state, photographic development can be performed by mixing the emulsion with a liquid developing composition.

The silver halide emulsion layer contacted with the spectral sensitizer as described above is processed by a conventional photographic processing. A known processing solution can be used in this case. The processing temperature is usually selected from 18° C. to 50° C., but may be lower than 18° C. or higher than 50° C.

With an increase in developing temperature, photographic density increases. Therefore, it is usually preferred to process at a pre-determined constant temperature. However, in place of processing at a constant temperature, a process may be employed wherein changes in photographic density due to changes in developing temperature are substantially prevented by using a neutralizing layer and a temperature compensation polymer layer. For example, the development can be performed on a silver halide emulsion layer formed adjacent a combined layer of an acid polymer layer as described in U.S. Pat. Nos. 4,056,394 and 4,061,496 and Japanese Patent Application OPI 72622/78.

Developing solutions used in the case of black-and-white photographic processing can contain known developing agents. As such developing agents, dihydroxybenzenes (e.g., hydroquinone), 3-pyrazolidones (e.g., 1-phenyl-3-pyrazolidone), aminophenols (e.g., N-methyl-p-aminophenol), 1-phenyl-3-pyrazolines, ascorbic acid, and heterocyclic compounds comprising a condensed 1,2,3,4-tetrahydroquinoline ring and an indolene ring as described in U.S. Pat. No. 4,067,872, etc., can be used singly or as a combination thereof.

The developing agent solutions can generally contain known preservatives, alkali agents, pH buffers, antifogging agents, and, if necessary, dissolution aids, color toning agents, development accelerators, surface active agents, defoaming agents, softening agents, hardening agents, viscosity-imparting agents, etc.

As a special aspect of development, a developing method which comprises treating a light sensitive material in which a developing agent is contained, e.g., in an emulsion layer, in an aqueous alkaline solution can be used. Of such developing agents, a hydrophobic type can be incorporated into an emulsion layer by latex dispersion, as disclosed in Research Disclosure, No. 169, RD-16928. Such development processing can also be used in combination with silver salt stabilization, e.g., with a thiocyanate(s).

In place of the above described black-and-white development process, a color development as is used in ordinary color photographic process can also be performed. In this case, a coupler is preliminarily dissolved in the developer or incorporated in the silver halide emulsion layer of a light sensitive element (see, for example, T. H. James, The Theory of The Photographic Process, 4th edition, pages 335 to 362, 1977, published by Macmillan Publishing Co., Ltd.).

By color development, areas contacted with the spectral sensitizer give blackening by silver and coloring by a coloring material, and hence in the color development, a higher optical density than blackening by silver alone is obtained. With developed areas obtained by color development, the light absorption due to blackening of silver and coloring due to dye formation can be measured by light of the light absorption wavelength(s) of the dyes.

After development, a stopping solution may be used in this invention and, as the stopping solution, an aqueous solution containing a compound capable of stopping development such as a pH reducing agent (e.g., a mineral acid, an organic acid, etc.) or a mercapto compound can be used. Also, when the fixing solution used is an acid fixing solution, i.e., having a sufficiently low pH for stopping the development, the stopping solution may be omitted.

As fixing solutions, those having compositions conventionally used in photographic processing can be employed, e.g., as fixing agents, organic sulfur compounds such as thiosulfates, thiocyanates and other organic sulfur compounds that are known as having a fixing effect can be employed. The fixing solution can also contain water soluble aluminum salts as a hardening agent.

This invention will now be described in detail with reference to the following examples to which this invention should not be limited, unless otherwise indicated.

EXAMPLE 1

Simultaneous measurement of labelled insulin and labelled human C-peptide (a) Preparation of insulin labelled with spectral sensitizer:

The carboxy group of the spectral sensitizer represented by the following formula (I):

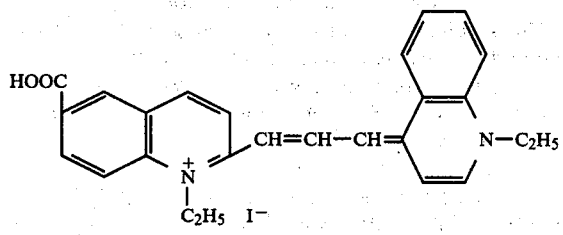

was chemically bonded to the terminal amino groups of pork insulin by the active ester method using a mixed acid anhydride. The resulting product was passed through a chromatographic column whereby purified insulin labelled with spectral sensitizer (I) was thus prepared and the fraction where one molecule of pork insulin was bonded to two molecules of spectral sensitizer was obtained.

The insulin thus labelled with spectral sensitizer (I) was adsorbed onto a silver chlorobromide emulsion to impart a maximum sensitivity thereto of around 685 nm.

(b) Preparation of human C-peptide labelled with spectral sensitizer:

The carboxy group of the spectral sensitizer of following formula (II) was chemically bonded to the tyrosine terminal amino group of human C-peptide having a tyrosine residue in the amino terminal by the mixed acid anhydride method.

The resulting product is purified by column chromatography whereby human C-peptide labelled with spectral sensitizer (II) was prepared.

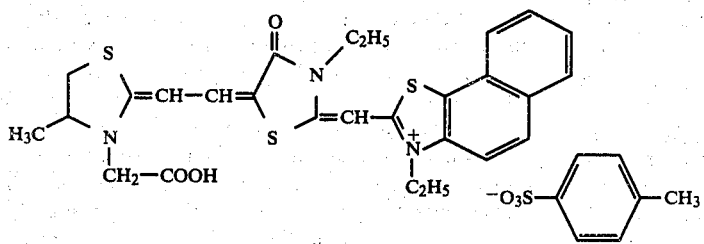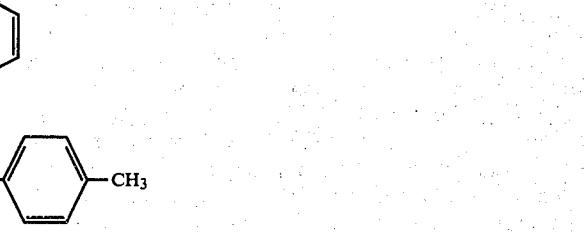

(II)

The human C-peptide thus labelled with spectral sensitizer (II) was adsorbed on a silver chlorobromide emulsion to impart a maximum sensitivity thereto of around 590 nm; such also imparted a small maximum sensitivity level at around 545 nm.

(c) Preparation of a film coated with silver chlorobromide emulsion:

Preparation of silver chlorobromide emulsion

To 300 ml of a 1% gelatin aqueous solution containing 49 g of KBr and 17 g. of NaCl at 70° C., 400 ml. of an aqueous solution containing 100 g. of $AgNO_3$ was added to form silver chlorobromide grains having an average grain size of $0.8\mu$ and then, after removing reaction by-products, 5 g. of gelatin and a suitable amount of a sulfur-containing sensitizer were added thereto and the mixture ripened; about 1 kg. of silver chlorobromide emulsion was obtained.

Preparation of a coated film (see FIG. 1)

On one side of a $120\mu$ thick polyester support (1), a gelatin aqueous solution containing suspended yellow colloidal silver was coated and dried to form an optical filter layer (2) having an optical density of 6.5 to light of a wavelength of 435 nm. Then, a coating composition prepared by adding a small amount of sodium dodecylbenzene sulfonate as a coating aid to 60 g. of a 10% aqueous solution of lime treated gelatin and 40 g. of a 10% aqueous solution of a copolymer of acrylic acid and vinyl pyrrolidone (monomer ratio of 5:95) was coated on the other side of the support and dried to form $4.5\mu$ thick subbing layer (3). On the resulting subbing layer, a composition prepared by adding a small amount of a viscosity increaser, a small amount of a coating aid and a small amount of a stabilizer for a silver halide emulsion (e.g., 6 ml. of a 0.1% 1-phenyl-5-mercaptotetrazole solution and/or a 5 ml. of a 1% 4-hydroxy-6-methyl-1,3,3a,7-tetrazaindene) to 100 g. of a silver chlorobromide emulsion prepared as above was coated and dried to form $4.0\mu$ thick emulsion layer (4). On the resulting emulsion layer, a composition prepared by adding a small amount of a viscosity increaser and a small amount of a coating aid to a 4% aqueous solution of lime treated gelatin was coated and dried to form a $0.8\mu$ thick filter layer (5). Filter layer (5) functions to prevent suspended ingredients contained in the reaction product after the immune reaction from directly coming into contact with the emulsion layer to cause fogging. Layer (5) also acts as a protecting layer which prevents scratching or rubbing during processing of the coated film from causing undesirable fog in the emulsion layer.

(d) Detection of two components using the emulsion coated film:

To 200 $\mu l$ of a 0.1 M tris-hydrochloric acid buffer solution (pH 8.5), a 100 $\mu l$ of an aqueous solution of insulin ($1.2 \times 10^{-8}$ to $4.0 \times 10^{-10}$ g/ml) labelled with spectral sensitizer (I) described above, a 100 $\mu l$ solution of human C-peptide labelled with spectral sensitizer (II), both of which were of various concentrations, and 100 $\mu l$ of saline were added to form different testing samples.

25 $\mu l$ of each testing sample was spotted in four places on an emulsion coated film prepared as above. Blank solutions containing only the saline and buffer solution as above were spotted in two places on the same film in a similar manner.

After spotting and permitting to stand for 10 mins. at 25° C., the two sample spots were exposed through an interference filter having a transmission maximum of 685 nm from the rear side of the coated film, and the remaining two sample spots were exposed through an interference filter having a transmission maximum of 600 nm using a xenon flash lamp from the rear side of the coated film. The two spots of blank solution were not exposed.

The exposed sample spots were then processed with a developer of the following composition for 10 mins. at 20° C., followed by processing with a conventional stopping solution and a fixing solution, water washing and drying.

| Developer | |
|---|---|
| Metol | 0.3 g |
| Sodium sulfite (anhydrous) | 38 g |
| Hydroquinone | 9 g |
| Sodium carbonate monohydrate | 45 g |
| Citric acid | 0.7 g |
| Potassium bisulfite (isomeric) | 1.4 g |
| Water to make | 1 liter |

The optical density of each spot was then measured through a red or yellow filter (the average value of two optical density measurements on each spot corresponding to each exposed area minus that of the blank gave concentration).

The results are given in Table I below.

TABLE I

| | Optical Density of Spots | | | |
|---|---|---|---|---|
| Concentration of Dye-Labelled Insulin $C_2^*$ (g/ml) | Concentration of Dye-labelled Insulin $C_1^*$ (g/ml) $\log C_1$ | | | |
| | $\overline{8.08}$ | $\overline{9.48}$ | $\overline{10.88}$ | $\overline{10.60}$ |
| $\log C_2$ | | | | |
| $\overline{8.08}$ | 2.58 | — | 0.49 | 0.00 |
| | 2.75 | — | 3.00 | 3.12 |
| $\overline{9.48}$ | — | 1.54 | — | — |
| | — | 1.62 | — | — |
| $\overline{10.88}$ | 2.56 | — | 0.33 | 0.00 |
| | 0.80 | — | 0.42 | 0.38 |
| $\overline{10.60}$ | 2.47 | — | 0.30 | 0.00 |
| | 0.31 | — | 0.00 | 0.00 |

Upper value: 685 nm exposed part $D_1$
Lower value: 600 nm exposed part $D_2$
*concentration in a solution of insulin labelled with dye (I) and of C-peptide labelled with dye (II).

From the optical density values given above (the blank optical density has beenr deducted), the method of least squares gave the following relations between $\log C_1$, $\log C_2$ and $D_1$, $D_2$.

$\log C_1 = 0.575 D_1 - 0.016 D_2 + \overline{10}.641$
$\log C_2 = -0.025 D_1 + 0.515 D_2 + \overline{10}.603$ These formulas were derived from Table I.

Next, a testing sample having known concentrations of insulin ($\log C_1 = \overline{9}.48$) and human C-peptide ($\log C_2 = \overline{9}.48$) was prepared in a manner similar to above and analyzed on the same film system by a method as above and the optical densities of insulin ($D_1 = 1.54$) and C-peptide ($D_2 = 1.62$) were obtained. These $D_1$ and $D_2$ values were substituted for $D_1$ and $D_2$ in the above formula and gave $\log C_1 = \overline{9}.50$ and $\log C_2 = \overline{9}.40$. The accuracy of the obtained data were then analyzed. Differences between concentrations of each testing sample and those calculated from the optical densities obtained by spotting these testing samples on the film were 0.03 (for $\log C_1$) and 0.08 (for $\log C_2$) when expressed as an unbiased estimate of population variance of logarithmic concentration. In other words, the concentrations of labelled insulin and labelled C-peptide may be measured in a simultaneous measuring system with accuracies of CV value $\pm 7\%$ and $\pm 20\%$, respectively.

EXAMPLE 2

Simultaneous measurement of insulin and human C-peptide immune reaction in the same reaction system:

(a) Reagents and Procedure:

(1) 200 μl of a 0.5 M borate buffer solution (pH 8.5) containing 1% BSA was weight in a test tube.

(2) 50 μl of anti-insulin guinea pig serum and 50 μl of anti-human C-peptide guinea pig serum were added.

(3) 100 μl of a testing sample was added.

(4) 100 μl of a 1% BSA solution containing insulin labelled with spectral sensitizer (I) and human C-peptide labelled with spectral sensitizer (II) were added in known concentrations.

(5) The system was allowed to stand for 48 hrs. at 4° C. (in the dark).

(6) 100 μl of anti-guinea pig γ-globulin rabbit serum was added.

(7) The system was allowed to stand for 24 hrs. at 4° C. (in the dark).

(8) The system was centrifuged for 30 mins. at 2500 g; the resulting supernatant was to be used for the following measurement.

(b) Measurement of the remaining labelled antigens contained in the supernatant:

(1) The supernatant prepared by procedure (a) was spotted in four places (25 μl per place) on the emulsion coated film prepared according to Example 1.

(2) A supernatant prepared by procedure (a) except that 200 μl of saline was substituted for solutions (3) and (4), was spotted in two places (25 μl per each) on the same film as a blank.

(3) The system was allowed to stand for 10 mins. at 25° C.

(4) Two spots of a testing sample were exposed through an interference filter having a transmission maximum of 685 nm and then the remaining two spots were exposed through an interference filter having a transmission maximum of 600 nm to the light from a xenon flash lamp from the rear side of the coated film.

(5) The coated film was developed, followed by stopping, fixing, water washing and drying as in Example 1.

(6) The optical density of each spot was measured through a red filter.

(7) The concentrations of labelled insulin and labelled human C-peptide in the supernatant were calculated from the optical densities in the same manner as in Example 1.

(8) In the same manner as above, the concentrations of labelled insulin and labelled human C-peptide in a supernatant prepared by the same procedure as in (a) above except that 100 μl of a mixed solution of various standard amounts of pork insulin and human C-peptide was substituted for the testing sample in solution (3) of (a) above were calculated and a calibration curve was made (FIG. 2: calibration curve for insulin; FIG. 3: calibration curve for human C-peptide).

(9) The concentrations of insulin and human C-peptide in the testing sample were determined using the calibration curves made by procedure (8) (FIGS. 2 and 3) and the amounts of labelled insulin and labelled human C-peptide obtained by procedure (7) were determined.

(c) As a testing sample, a saline solution containing 2.0 ng/ml of insulin and 5.0 ng/ml of human C-peptide was prepared. The concentrations of insulin and human C-peptide were measured as in procedures (a) and (b)

above. The measurement value of 2.5 ng/ml was obtained for insulin and 4.0 ng/ml for human C-peptide, respectively. These measurement values were well consistent with the given concentrations of insulin and human C-peptide.

While the invention has been described in detail and with reference to specific embodiments thereof, it will be apparent from one skilled in the art that various changes and modifications can be made therein without departing from the spirit and scope thereof.

What is claimed is:

1. A method for the simultaneous immunochemical assays of trace components in a sample comprising:
   (a) competitively reacting
      at least two different and differently labeled antigens or at least two different and differently labeled antibodies, the labels being spectral sensitizing dyes differing from one another in their absorption spectra and at least two antigens or at least two antibodies in the sample being assayed, respectively, for limited binding sites on corresponding antibodies or corresponding antigens, respectively;
   (b) contacting either the reaction products resulting from (a) or the unreacted reactants also of (a) with silver halide;
   (c) exposing the silver halide resulting from (b) to light having the wavelengths corresponding to the absorption spectra of the spectral sensitizing dyes;
   (d) developing the exposed silver halide reslting from (c);
   (e) measuring the optical densities resulting from (d); and
   (f) determining the amounts of the at least two antigens or the at least two antibodies in the sample by correlations with the optical densities measured in (e).

2. The method for immunochemical measurement of two kinds of trace components as in claim 1 wherein an antigen of antibody is labelled with a spectral sensitizing dye having a light sensitive maximum wavelength longer than 630 nm and another antigen or antibody is labelled with another specrtral sensitizing dye having a light sensitive maximum wavelength of shorter than 630 nm, the difference between the two maximum wavelengths being more than 50 nm.

3. The method for immunochemical measurement of two kinds of antigens or antibodies in the same reaction system as in claim 1 wherein at least one drop of the competitive reaction product or the remaining unreacted substance is applied to at least two areas on a coating comprising at least one light sensitive silver halide emulsion layer, wherein one of the two areas is exposed to light through a filter transmitting light of the wavelength longer than 500 nm and the other is exposed through a filter transmitting light of a wavelength of longer than 630 nm, whereafter the areas are developed and the optical density of the areas are measured followed by calculation of the resulting black density.

4. The method for immunochemical measurement of two kinds of antigens or antibodies in the same reaction system as in claim 2 or 3 wherein two drops of the competitive reaction product or the remaining unreacted substance are dropped in each of at least two areas on a coating comprising at least one light sensitive silver halide emulsion layer, wherein one of the two areas is exposed to light through a filter having a transmission maximum wavelength in the range of from 500 nm to 630 nm, and the other is exposed through a filter transmitting light of a wavelength longer than 630 nm, whereafter the areas are developed and the optical density of the areas measured followed by calculation of the resulting black density.

5. The method for immunochemical measurement as in claim 1, 2 or 3 wherein the two kinds of antigens or antibodies to be measured are trace components in serum.

6. The method for immunochemical measurement as in claim 1, 2 or 3 wherein a single kind of the second antibody is reacted, said second antibody having reactivity common to at least two kinds of antibodies or antigens which specifically react with each antigens or antibodies.

* * * * *